(12) United States Patent
Edgett et al.

(10) Patent No.: US 6,508,780 B1
(45) Date of Patent: Jan. 21, 2003

(54) LATERALLY LOADED INSERTION DEVICE

(75) Inventors: Keith Edgett, Ramsey, NJ (US); Dane R. Jackson, Bloomingdale, NJ (US); Jessica Lemay, Paramus, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/038,552

(22) Filed: Jan. 4, 2002

(51) Int. Cl.$^7$ ................................................. A61F 13/20
(52) U.S. Cl. ............................................................. 604/15
(58) Field of Search ........................... 604/11–18, 57, 604/59, 60, 311

(56) References Cited

U.S. PATENT DOCUMENTS

| | | | |
|---|---|---|---|
| 2,351,836 A | 6/1944 | Popper | 128/285 |
| 2,450,138 A | 9/1948 | Harwood | 128/263 |
| 3,884,233 A | * 5/1975 | Summey | |
| 4,159,719 A | 7/1979 | Haerr | 128/260 |
| 4,210,140 A | 7/1980 | James et al. | 128/266 |
| 4,421,504 A | 12/1983 | Kline | 604/12 |
| 4,871,094 A | * 10/1989 | Gall et al. | |
| 5,312,333 A | * 5/1994 | Churinetz et al. | |
| 6,325,789 B1 | * 12/2001 | Janzen et al. | |

FOREIGN PATENT DOCUMENTS

| | | |
|---|---|---|
| CA | 684364 | 4/1964 |
| FR | 726606 | 3/1955 |

* cited by examiner

Primary Examiner—Dennis Ruhl
(74) Attorney, Agent, or Firm—Ohlandt, Greeley, Ruggiero & Perle, LLP

(57) ABSTRACT

The present invention provides a tampon applicator adapted to allow a pledget to be laterally loaded into the barrel of the applicator. By laterally loading the pledget, the applicator may include pre-formed petals on the insertion end of the barrel and/or a fingergrip having a reduced diameter. The applicator may be formed from any suitable material, such as, for example, biopolymer, paper, paperboard, paper slurry, plastic, thermoplastic polymer, thermosetting polymer, or any combinations thereof.

33 Claims, 5 Drawing Sheets

LATERALLY LOADED INSERTION DEVICE

BACKGROUND OF THE INVENTION

1. Field of the Invention

The present invention relates to an insertion device, such as a catamenial tampon applicator. More particularly, the present invention relates to a tampon applicator that is laterally loaded with an absorbent pledget.

2. Description of the Prior Art

The barrel of present commercial tampons having a plastic applicator are typically manufactured as one-piece molded objects, such as those of Kotex Securitye tampons and Playtex Gentle Glides tampons. The barrel of present commercial cardboard applicator tampons are formed from either convolutely wound cardboard, such as o.b. applicator tampons, or spiral-wound cardboard, such as Tampax® tampons.

In order to improve comfort during use, an applicator may be formed with petals on the insertion end of the applicator.

Additionally, some applicators have a fingergrip and a plunger of a diameter reduced from that of the applicator barrel. This feature has been found not only to render the tampon applicator more grippable, but it is also more aesthetically preferred by consumers.

For current reduced diameter fingergrip tampon applicators, the tampon pledget must be loaded into the insertion end of the applicator due to the smaller opening at the fingergrip end. As a result, these tampons are restricted from bottom or plunger end loading of the absorbent pledget. This requires the petals of the applicator, if any, to be post-formed to their final shape after the pledget has been loaded with an absorbent pledget. Post-forming of petals requires the material to be plasticized. Typically, plastic petals are plasticized by heat and are shaped by the use of an external forming die.

Cardboard petals are more difficult to plasticize and require the additional use of an internal mandrel. Usual methods involve heating the tip to volatilize the water (either existing or supplemental moisture) and then forcing the petal into shape using an internal mandrel in conjunction with the external die. The internal mandrel has a diameter that is approximately the same as the barrel, and consequently would not be able to enter through a reduced diameter fingergrip area. Thus, the necessity of the internal mandrel to shape the petal tip has precluded the manufacture of a reduced diameter fingergrip area on a cardboard applicator.

With current tampon assembly methods, it is only feasible to have one highly enlarged plunger end prior to assembly of the plunger into the barrel, because the other end of the plunger must fit through the fingergrip area, whether the plunger is inserted into the applicator through the bottom or the top of the barrel. The plunger end that fits through the fingergrip area can be flared after applicator assembly, but this approach limits the design possibilities of the flare and increases manufacturing difficulties.

Therefore, there is a need for a tampon applicator, and more particularly a cardboard applicator, having a reduced diameter fingergrip and/or plunger that can be manufactured such that petals can be pre-formed or integrated on the insertion end of the applicator barrel, prior to loading an absorbent pledget into the applicator barrel.

SUMMARY OF THE INVENTION

It is an object of the present invention to provide a tampon applicator adapted to allow an absorbent pledget to be side or laterally loaded into the barrel of the applicator.

It is another object of the present invention to provide such a tampon applicator having petals pre-formed on the insertion end of the applicator barrel.

It is still another object of the present invention to provide such a tampon applicator having a fingergrip.

It is a further object of the present invention to provide such a tampon applicator having a fingergrip with a reduced diameter compared to the diameter of the applicator barrel.

It is still a further object of the present invention to provide a method of making a tampon applicator having an absorbent pledget laterally loaded into the barrel of the applicator.

These and other objects and advantages of the present invention will be appreciated by a tampon applicator adapted to allow an absorbent pledget to be laterally loaded into the barrel of the applicator. By laterally loading the pledget, the applicator may include pre-formed petals on the insertion end of the barrel and/or a fingergrip having a reduced diameter. The applicator may be formed from any suitable material, such as, for example, biopolymer, paper, paperboard, paper slurry, plastic, thermoplastic polymers, thermosetting polymers, or any combinations thereof.

DETAILED DESCRIPTION OF THE INVENTION

The present invention provides a formed applicator barrel that is adapted to be laterally loaded with an absorbent pledget, i.e. the pledget is loaded through neither the insertion end or the removal end of the applicator, but rather is placed inside a barrel that is at least partially opened along one side. The formed applicator barrel may also include pre-formed petals on the insertion end of the applicator barrel and/or a fingergrip on the removal end of the applicator.

By forming the applicator in this manner, it allows for many adjustments to be made to the applicator in particular, and the tampon as a whole, that are not possible with the current approaches to forming applicators and loading pledgets. For example, it allows the petals to be pre-formed and the fingergrip to have a reduced diameter simultaneously because it eliminates the need for an opening in the end of the applicator large enough to accept the pledget.

It is believed that reduced diameter fingergrips are perceived by consumers to be more grippable and aesthetically preferred. Pre-formed petals are favored from a production standpoint since more accuracy and symmetry is ensured. Also, some materials, such as paper slurry, are resistant to post-forming and require the use of an internal mandrel, which is currently difficult in conjunction with a reduced diameter fingergrip. Incorporating pre-formed petals with a reduced diameter fingergrip creates an optimal combination of aesthetics and quality.

Figure 1:
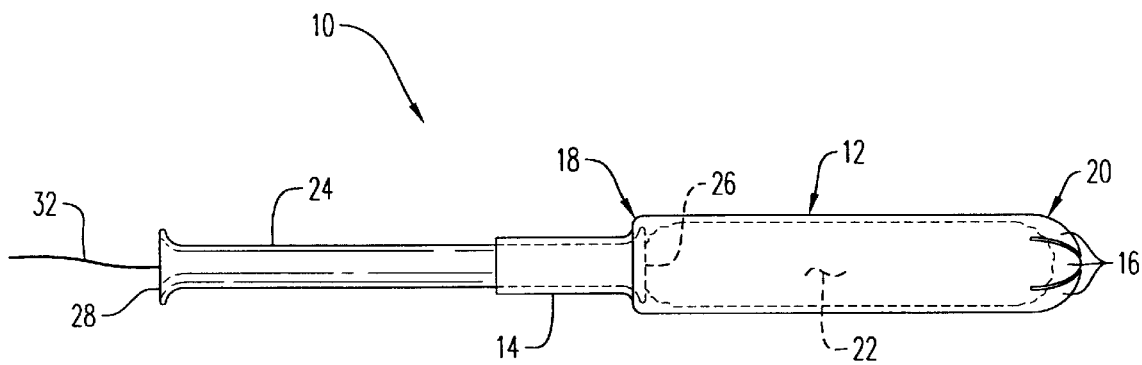
FIG. 1 is a plan view of an assembled tampon applicator according to all embodiments of the present invention.

Referring to FIG. 1, an assembled tampon applicator according to the present invention is represented by reference numeral 10. The applicator 10 has a barrel or applicator barrel 12 with a plunger end 18 and an insertion end 20, and a plunger 24. The barrel 12 is formed such that a pledget 22 is side or laterally loaded in the barrel. It is preferred that assembled applicator barrel 12 have petals 16 pre-formed on insertion end 20 to enhance user comfort. Typically, applicator barrel 12 will have about two to about twelve petals 16 pre-formed on insertion end 20. More preferably, applicator barrel 12 will have about two to about six pre-formed petals 16. Applicator 10 may also have a reduced diameter fingergrip 14 and, preferably, plunger 24 also has a reduced diameter. Pledget 22 has a removal string 32.

Figure 2:
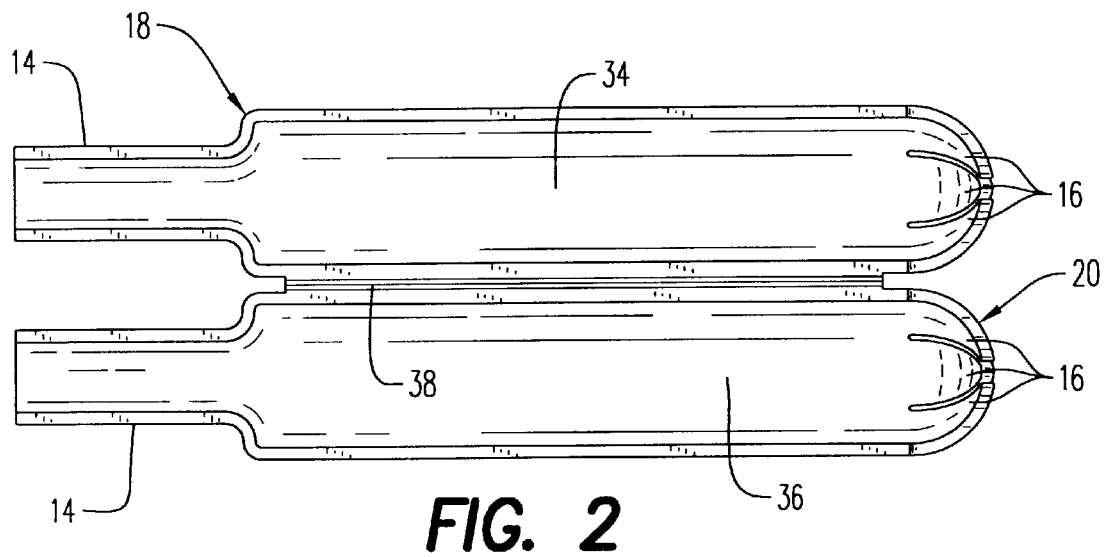
FIG. 2 is a plan view of a two-piece, movably connected tampon applicator barrel according to one embodiment of the present invention.
Figure 3:
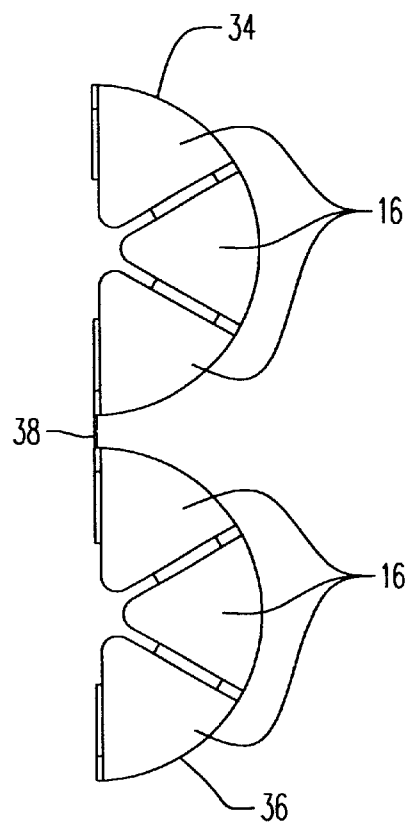
FIG. 3 is an end view of the insertion end of the tampon applicator barrel of FIG. 2.

Referring to FIGS. 2 and 3, one embodiment of the applicator barrel 12 of the tampon applicator of the present invention is depicted. Applicator barrel 12 may be a single molded barrel having a first barrel portion 34 and a second barrel portion 36, which is essentially a mirror image of and similar in shape to barrel portion 34. When the first barrel portion 34 and second barrel portion 36 are combined or connected, they form a cross-section that may be generally circular, ovoid, elliptical, or any combinations thereof. First barrel portion 34 is movably connected to second barrel portion 36 by one or more connectors 38 along one side of each barrel portion. Suitable connectors 38 include, for example, a mechanical hinge, a living hinge, or any combinations thereof. Preferably, one or more connectors 38 is a living hinge, akin to a clamshell.

Each barrel portion 34, 36 preferably has pre-formed petals 16 that enhance user comfort during insertion of the assembled applicator 10. The total number of petals desired on the assembled applicator 10 can be divided between first barrel portion 34 and second barrel portion 36 in any manner. Also, for greater ease of insertion, first barrel portion 34 and second barrel portion 36 both have a reduced diameter fingergrip 14 integrally formed at plunger end 18 of barrel portions 34, 36 of applicator 10.

Figure 4:
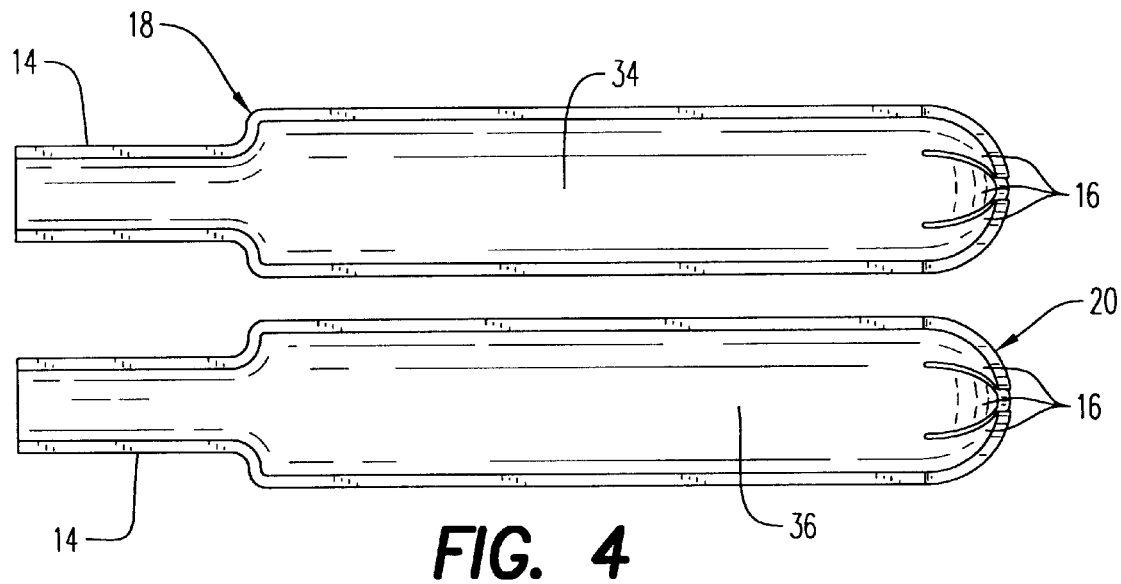
FIG. 4 is a plan view of a two-piece, non-connected tampon applicator barrel according to a second embodiment of the present invention.
Figure 5:
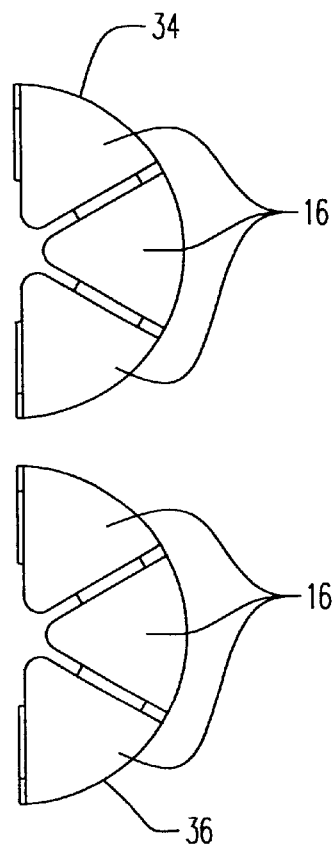
FIG. 5 is an end view of the insertion end of the tampon applicator barrel of FIG. 4.

Referring to FIGS. 4 and 5, in a second embodiment of the tampon applicator of the present invention, applicator 10 has a first barrel portion 34 and a separate, non-connected second barrel portion 36. Preferably, second barrel portion 36 is essentially the mirror image of first barrel portion 34. In addition, each barrel portion 34, 36 has petals pre-formed on insertion end 20. Again, for greater ease during insertion of applicator 10, first barrel portion 34 and second barrel portion 36 both have a reduced diameter fingergrip 14 integrally formed at plunger end 18.

The grippability of fingergrip 14 may be enhanced by forming at least one gripping structure, and preferably a plurality of gripping structures, in or on the outer surface of fingergrip 14. Fingergrip 14 may be textured in addition to having at least one gripping structure.

The gripping structures may be molded or formed in any number and/or configuration suitable for creating enhanced grippability of tampon applicator 10. The gripping structures may be molded such that they extend above the outer surface of fingergrip 14, they extend below the outer surface of the fingergrip, the tip or upper edge of the gripping structure is aligned with the outer surface of the fingergrip, or any combinations thereof. Suitable shapes or configurations for gripping structures include, for example, one or more arcs, circles, concave, cones, convex, diamonds, grooves, lines, louvers, ovals, polygons, protuberances, rectangles, ribs, slits, squares, treads, triangles, or any combinations thereof.

Figure 6:
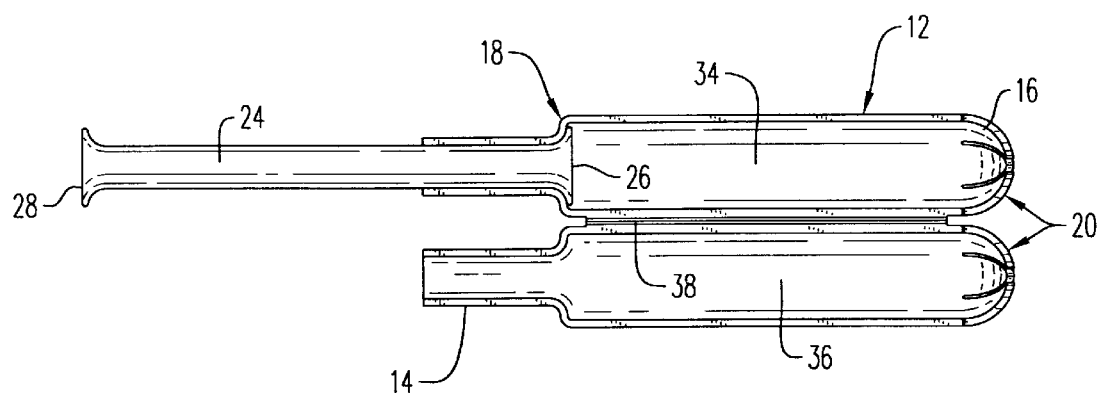
FIG. 6 is a plan view of th e tampon applicator of FIG. 2 with a plunger positioned in one piece of the two-piece barrel.
Figure 7:
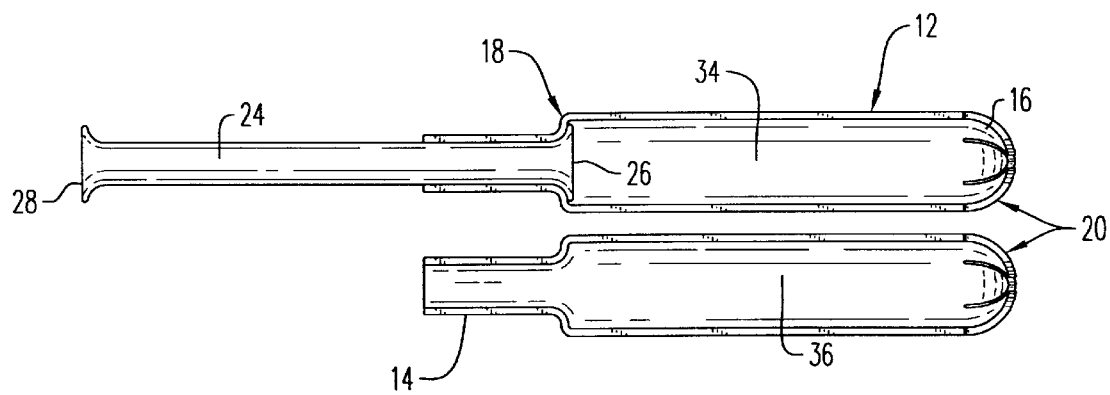
FIG. 7 is a plan view of the applicator barrel of FIG. 4 with a plunger positioned in one piece of the two-piece, non-connected applicator barrel.

Referring to FIGS. 6 and 7, the tampon applicator barrels 12 of FIGS. 2 and 4 are now depicted with plunger 24 positioned in first barrel portion 34. Plunger 24 has a pledget-contacting end 26 and a free or removal end 28. It is an advantage of the present invention to be able to modify the dimensions of the ends of plunger 24. For example, increasing the size of pledget-contacting end 26 of plunger 24 is useful because it distributes the force from the plunger over a larger area of the pledget, which is especially useful if the pledget is not rigid. Having plunger 24 with a pledget-contacting end 26 that is larger than that of the base opening of barrel 12 is also beneficial because it prevents separation of the plunger from the barrel, a point of frustration for many consumers.

Preferably, removal end 28 is a flared end. A flared removal end provides the benefit of a comfortable finger-rest during insertion of tampon applicator 10. With the open-sided barrel 12 of the present invention, plunger 24 is placed inside applicator 10 prior to forming assembled barrel 12, enabling both plunger ends 26, 28 to have an increased size or flare, as well as the barrel having a reduced diameter fingergrip and pre-formed petals.

Figure 8:
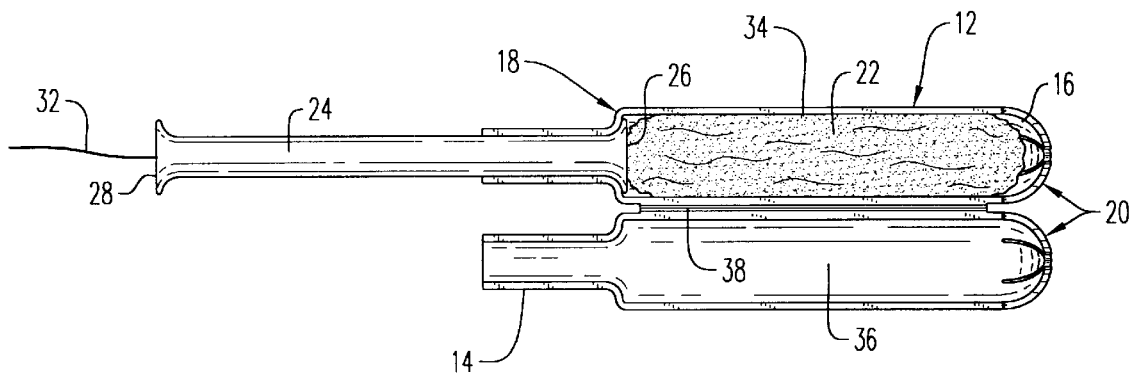
FIG. 8 is a plan view of the tampon applicator of FIG. 6 with an absorbent pledget laterally loaded into one piece of the two-piece, movably connected applicator barrel.
Figure 9:
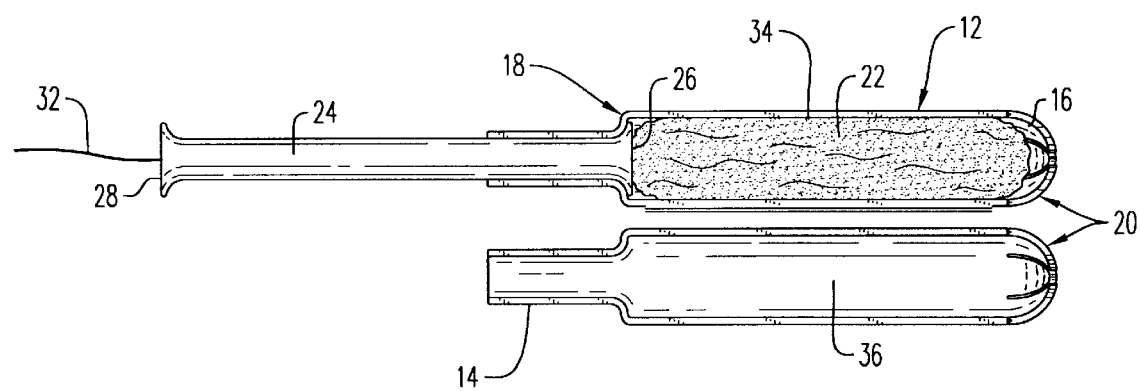
FIG. 9 is a plan view of the tampon applicator of FIG. 7 with an absorbent pledget laterally loaded into one piece of the two-piece, non-connected barrel.

Referring to FIGS. 8 and 9, the tampon applicator assembly of FIGS. 6 and 7 are now depicted with absorbent pledget 22 laterally or side loaded into first barrel portion 34. After laterally loading absorbent pledget 22, first barrel portion 34 and second barrel portion 36 are connected and secured together.

There are several possibilities for connectably securing first barrel portion 34 with second barrel portion 36. Suitable connectors include, for example, adhesive, melt welding, snapping the pieces together (i.e. interference fit), or any combinations thereof. Preferably, the first and second barrel portions 34, 36 are secured by an adhesive.

The side-loaded tampon applicator 10 may be formed from any formable material known in the art. Suitable formable material includes, for example, biopolymer, paper, paperboard, paper slurry, plastic, thermoplastic polymer, thermosetting polymer, or any combinations thereof.

In addition to incorporating a reduced diameter fingergrip 14 with pre-formed petals 16, it is possible to form applicator 10 in a shape that would otherwise be impossible to create in conjunction with a reduced diameter fingergrip and/or pre-formed petals. By way of example, barrel 12 itself may be tapered towards the tip or insertion end 20, or it could have varying diameters throughout its entire length. The cross-section of the barrel may be, for example, circular, ovoid, elliptical, or any combinations thereof. These more complex designs offer possibilities that are precluded by the standard forming processes, since the mold mandrel would not have to be removed through a smaller opening.

This method of barrel formation also provides the ability to create a more intricate surface topography. For example, any variety of size, shape, style, and number of protuberances can be formed into the applicator, creating both internal and external features. These features could include ridges inside the barrel that reduce the contact area between the barrel and plunger and the barrel and pledget, thus reducing ejection force.

A laterally loaded or side loaded barrel 12 allows for modifications to and treatments of the barrel itself, which are more difficult to execute with current molding techniques. With the inner surface of barrel 12 exposed during the tampon assembly process, it becomes easier to incorporate surface treatments into the production process. For example, the inner surface of barrel 12 may be treated with a friction-reducing coating, or with microcapsules containing fragrance, lubricant, medicinal composition, or other materials that would be activated when pledget 22 was expelled from applicator 10.

Suitable surface treatment materials for treating any surface of barrel 12 and/or plunger 24 to enhance strength and/or reduce surface friction include, for example, cellophane, cellulose, epoxy, lacquer, nitrocellulose, nylon, plastic, silicone, polyester, polylactide, polyolefin, polyvinyl alcohol, polyvinyl chloride, wax, or any combinations thereof.

The present invention having been thus been described with particular reference to the preferred forms thereof, it will be obvious that various changes and modifications may be made therein without departing from the spirit and scope of the present invention as defined in the appended claims.

Wherefore we claim:

1. A tampon applicator comprising:
   a first barrel portion; and
   a second barrel portion adapted to be connected to said first barrel portion,
   wherein said first and second barrel portions when not connected are adapted to laterally receive a pledget.

2. The tampon applicator of claim 1, wherein said first barrel portion is substantially similar in shape to said second barrel portion so that said first barrel portion and second barrel portion form an enclosure for the pledget.

3. The tampon applicator of claim 1, wherein said first barrel portion and said second barrel portion are formed from a material selected from the group consisting of biopolymer, paper, paperboard, paper slurry, plastic, and any combinations thereof.

4. The tampon applicator of claim 1, wherein said first barrel portion, said second barrel portion, or both said first and second barrel portions have thereon a surface treatment material.

5. The tampon applicator of claim 4, wherein said first barrel portion, said second barrel portion, or both said first and second barrel portions are externally coated, internally coated, or both externally and internally coated with said surface treatment material.

6. The tampon applicator of claim 5, wherein said surface treatment material is selected from the group consisting of cellophane, cellulose, epoxy, lacquer, nitrocellulose, nylon, plastic, silicone, polyester, polylactide, polyolefin, polyvinyl alcohol, polyvinyl chloride, wax, and any combinations thereof.

7. The tampon applicator of claim 1, wherein said first barrel portion is movably connected to said second barrel portion by a hinge selected from the group consisting of mechanical, living, and any combination thereof.

8. The tampon applicator of claim 1, wherein said first barrel portion and said second barrel portion each have an insertion end and a removal end opposite the insertion end.

9. The tampon applicator of claim 8, further comprising one or more pre-formed petals on said insertion end of said first barrel portion and said second barrel portion.

10. The tampon applicator of claim 8, further comprising a fingergrip formed at said removal end of said first barrel portion and said second barrel portion.

11. The tampon applicator of claim 10, wherein said fingergrip has a reduced diameter.

12. The tampon applicator of claim 11, wherein said fingergrip has one or more gripping structures.

13. The tampon applicator of claim 12, wherein said one or more gripping structures are selected from the group consisting of arcs, circles, concavities, cones, convexities, diamonds, grooves, lines, louvers, ovals, polygons, protuberances, rectangles, ribs, slits, squares, treads, triangles, and any combinations thereof.

14. The tampon applicator of claim 1, further comprising a plunger having a barrel end and a removal end opposite the barrel end.

15. The tampon applicator of claim 14, wherein said plunger has a reduced diameter.

16. The tampon applicator of claim 15, wherein said plunger has an increased diameter at said removal end adapted to provide a secure finger rest.

17. The tampon applicator of claim 15, wherein said plunger has an increased diameter at said barrel end.

18. The tampon applicator of claim 14, wherein said plunger is formed from a material selected from the group consisting of biopolymer, papaer, paperboard, paper slurry, plastic, or any combinations thereof.

19. A method of forming a tampon applicator adapted to be laterally loaded with an absorbent pledget comprising the steps of:
   (a) providing a first barrel portion having a first insertion end and a removal end opposite the first insertion end, and a second barrel portion having a second insertion end and a removal end opposite the second insertion end;
   (b) loading a pledget in said first barrel portion or said second barrel portion; and
   (c) securing said first barrel portion to said second barrel portion to enclose the pledget.

20. The method of claim 19, further comprising, after step (a), a step of placing a plunger in said removal end of said first barrel portion or said second barrel portion.

21. The method of claim 19, further comprising, after step (b), a step of placing a plunger in said removal end of said first barrel portion or said second barrel portion.

22. The method of claim 19, wherein said first barrel portion is movably connected to said second barrel portion by a hinge selected from the group consisting of mechanical, living, and any combination thereof.

23. The method of claim 19, wherein said first barrel portion, said second barrel portion and said plunger are formed from a material selected from the group consisting of biopolymer, plastic, paper, paperboard, paper slurry, and any combinations thereof.

24. The tampon applicator of claim 19, wherein said first barrel portion, said second barrel portion, or both said first and second barrel portions have thereon a surface treatment material.

25. The tampon applicator of claim 24, wherein said first barrel portion, said second barrel portion, or both said first and second barrel portions are externally coated, internally coated, or both externally and internally coated with said surface treatment material.

26. The tampon applicator of claim 25, wherein said surface treatment material is selected from the group consisting of cellophane, cellulose, epoxy, lacquer, nitrocellulose, nylon, plastic, silicone, polyester, polylactide, polyolefin, polyvinyl alcohol, polyvinyl chloride, wax, and any combinations thereof.

27. The method of claim 19, wherein said first barrel portion and said second barrel portion are substantially similar in shape.

28. The method of claim 19, wherein said first barrel portion and said second barrel portion have one or more pre-formed petals on said first insertion end portion and said second insertion end portion.

29. The method of claim 19, wherein said first barrel portion is secured to said second barrel portion by a securing means selected from the group consisting of adhesive, melt welding, interference fit, and any combinations thereof.

30. A laterally loaded tampon applicator formed by the method of claim 19, wherein the pledget is an absorbent pledget.

31. The tampon applicator of claim 1, wherein said first barrel portion and said second barrel portion are formed from a plastic material selected from the group consisting of thermoplastic polymer, thermosetting polymer, and any combinations thereof.

32. The tampon applicator of claim 14, wherein said plunger is formed from a plastic material selected from the group consisting of thermoplastic polymer, thermosetting polymer, and any combinations thereof.

33. The method of claim 19, wherein said first barrel portion, said second barrel portion and said plunger are formed from a plastic material selected from the group consisting of thermoplastic polymer, thermosetting polymer, and any combinations thereof.

* * * * *

UNITED STATES PATENT AND TRADEMARK OFFICE
CERTIFICATE OF CORRECTION

| | |
|---|---|
| PATENT NO. | : 6,508,780 B1 |
| APPLICATION NO. | : 10/038552 |
| DATED | : January 21, 2003 |
| INVENTOR(S) | : Edgett et al. |

It is certified that error appears in the above-identified patent and that said Letters Patent is hereby corrected as shown below:

Column 6, line 52, claim 23 is now dependent upon "claim 19", and should depend from --claim 21--.

Signed and Sealed this

Eighth Day of April, 2008

JON W. DUDAS
*Director of the United States Patent and Trademark Office*